United States Patent [19]

Van Tonder

[11] Patent Number: 5,130,135
[45] Date of Patent: Jul. 14, 1992

[54] PESTICIDAL FORMULATIONS

[75] Inventor: Stephanus J. Van Tonder, Transvaal, South Africa

[73] Assignee: Smithkline Beecham plc, Middlesex, United Kingdom

[21] Appl. No.: 569,788

[22] Filed: Aug. 17, 1990

[30] Foreign Application Priority Data

Aug. 18, 1989 [ZA] South Africa .................. 89/6322

[51] Int. Cl.⁵ .............................................. A01N 25/00
[52] U.S. Cl. ................................... 424/405; 424/406; 424/407; 514/136; 514/521
[58] Field of Search ............... 424/405, 406, 407; 514/136, 521

[56] References Cited

U.S. PATENT DOCUMENTS

| 4,341,760 | 7/1982 | Matthewson et al. | 424/45 |
| 4,357,348 | 11/1982 | Kasamatsu et al. | 424/300 |
| 4,443,438 | 4/1984 | Kasamatsu et al. | 424/200 |
| 4,659,739 | 4/1987 | Yoshioka et al. | 514/555 |
| 4,696,938 | 9/1987 | Le | 514/393 |
| 4,742,056 | 5/1988 | Farooq et al. | 514/229.2 |
| 4,780,459 | 10/1988 | Matthewson | 514/136 |
| 4,897,386 | 1/1990 | Matthewson | 514/108 |
| 4,985,461 | 1/1991 | Hsu et al. | 514/615 |

FOREIGN PATENT DOCUMENTS 508292 6/1980 Australia.
0249409 12/1987 European Pat. Off..
198673 3/1985 New Zealand.

Primary Examiner—Thurman K. Page
Assistant Examiner—Louis A. Piccone
Attorney, Agent, or Firm—Janice E. Williams; Stuart R. Suter; Edward T. Lentz

[57] ABSTRACT

This invention relates to an animal pour-on pesticidal formulation which comprises at least one pesticide selected from the group consisting of the synthetic pyrethroids, preferably cypermethrin, the organophosphates and the amidines, and at least one vegetable oil consisting of glycerides of carboxylic acids with carbon chain lengths of more than 14 carbon atoms e.g. sunflower oil, as carrier for the pesticide which carrier constitutes at least 70% m/v of the formulation. The formulation may optionally further include a synergist, preferably piperonylbutoxide and solvents such as diacetone alcohol and dibutylphthalate.

8 Claims, 1 Drawing Sheet

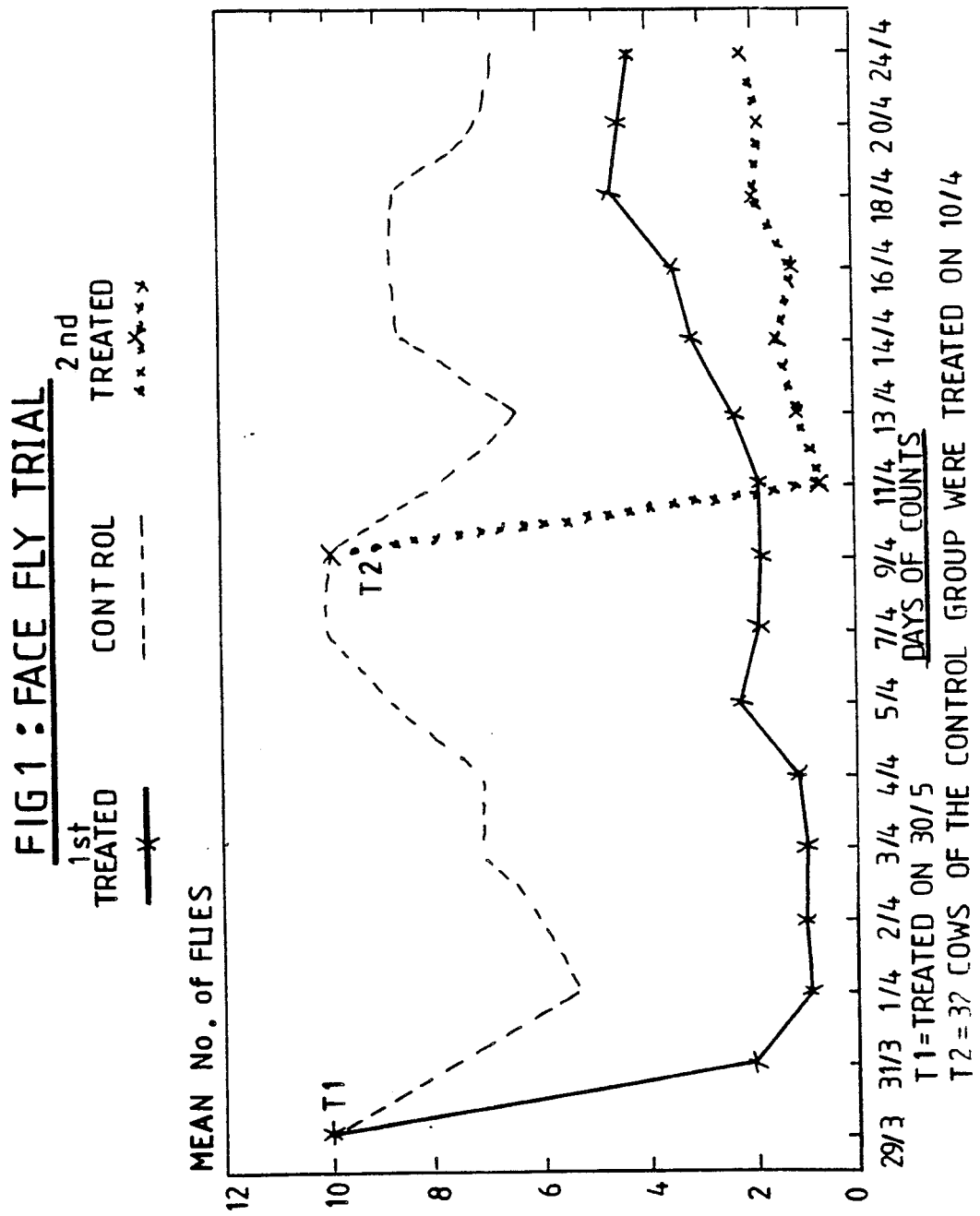

PESTICIDAL FORMULATIONS

FIELD OF THE INVENTION

This invention relates to pesticidal formulations. It relates in particular to an animal pour-on pesticidal formulation suitable for use as an ectoparasiticidal formulation in combatting ectoparasites such as ticks, flies, lice, midges and sand tampans on animals such as cattle, sheep, goats, pigs, horses and the like.

BACKGROUND OF THE INVENTION

Numerous ectoparasiticidal formulations are known in the art and several of these contain synthetic pyrethroids as active ingredients. Most, if not all, of the pyrethroids are known to be very active against a broad field of insects but are also known to exhibit a high degree of irritancy when applied to the skin of an animal. The many patent applications filed in various parts of the world in respect of pyrethroid based pour-on formulations which differ essentially only on their carrier systems bears witness to the search for more appropriate carrier systems.

OBJECT OF THE INVENTION

It is an object of the invention to provide pyrethroid containing pour-on formulations which have improved properties over known formulations.

DESCRIPTION OF THE INVENTION

According to the invention, there is provided an animal pour-on pesticidal formulation, which comprises at least one pesticide; and
at least one vegetable oil consisting of glycerides of carboxylic acids with carbon chain lengths containing more than 14 carbon atoms as a carrier for the pesticide, with the carrier being present in a proportion of at least 70% m/v in the formulation.

By "% m/v" or "mass volume to percentage" as used in this specification is meant grams of constituent or component in 100 ml of formulation.

The formulation of the invention may be applied externally or topically in localized fashion to an animal to be treated, eg. along the back of the animal. The oil-based carrier ensures good spreading of the pesticide over substantially the entire pelt or skin of the animal. In addition, the high proportion of the carrier present, i.e. 70% m/v or more, ensures that the pesticide is sufficiently diluted to have little or no skin irritation.

The pesticide may be a synthetic pyrethroid, and may be selected from the group consisting of alphamethrin, allethrin, barthrin, bioresmethrin, biopermethrin, cismethrin, cyclethrin, cypermethrin, cyhalothrin, cyfluthrin, cyphenothrin, deltamethrin, dimethrin, fenpropanate, fenvalerate, flumethrin, fluvalinate, indothrin, permethrin, phenothrin, phthalthrin, resmethrin, tetramethrin, sumithrin, tralomethrin and tralocythrin. The synthetic pyrethroid of choice is cypermethrin and more particularly a unique artificially prepared cypermethrin which contains more than 40%, and preferably about 48% of the (1R cis)S and (1S cis)R enantiomer isomer pair of alpha-cyano-3-phenoxybenzyl-3-(2,2-dichlorovinyl)-2,2-dimethylcyclopropane carboxylate, which enantiomer isomer pair is known in the field as alphamethrin.

It should be explained that cypermethrin consists of a mixture of two geometrical trans isomers and two geometrical cis isomers. Each of these isomers is a racemic mixture of two optical isomers [i.e. a total of eight isomers]. Alphamethrin consists of a racemic mixture of the two optical isomers known as the (1R cis)S and the (1S cis)R enantiomers. The ratio of cis to trans isomers in the cypermethrin used in practicing this invention is 45:55. By mixing cypermethrin with alphamethrin in the ratio of 2:1 a unique artificial isomeric mix that is not normally obtainable through synthesis is obtained, namely, one wherein the (1R cis)S and (1S cis)R enantiomer isomer pair constitutes about 48% of the total of all isomers of alpha-cyano-3-phenoxybenzyl-1-(2,2-dichlorvinyl)-2,2-dimethylcyclopropane carboxylate present in the mixture. This artificial combination is hereinafter referred to as "alphamethrin enriched cypermethrin".

Additionally, the insecticide may include an organophosphate, such as tetrachlorvinphos or diazinon, and/or an amidine, which may be selected from the group consisting in cymiazol, amitraz and chlordimeform.

Tetrachlorvinphos has growth regulatory properties while diazinon has larvacidal and ovicidal properties which are highly desirable in a formulation of this nature.

The vegetable oil may be pure sunflower seed oil. However, it can instead be any other suitable vegetable oil having properties similar to pure sunflower seed oil.

The formulation may comprise at least one solvent in which the pesticide is soluble.

When the pesticide is a synthetic pyrethroid and/or organophosphate, the solvent may be a polar solvent. The polar solvent, when present, may comprise less than 20% m/v of the formulation. The polar solvent should characteristically be a solvent of high boiling point [>150° C.] and high solvating power with respect to the chosen pyrethroid and organophosphate. The solvent should also have the effect of lowering the viscosity of the final formulation product. The ideal solvent for the present formulation is diacetone alcohol.

In addition, the formulation may include a fly and midge repellant which preferably also acts as a co-solvent. The repellant may be selected from the group consisting of dibutylphthalate, stabilene and the MGK insect repellants as supplied by McLaughlin Gormley King.

The mass proportion of pyrethroid to solvent may be between 1:2 and 1:10, typically about 1:5, while the mass ratio of organophosphate, when present, to solvent may also be between 1:2 and 1:10, typically about 2:5. The mass ratio of pyrethroid to oil may be between 1:46 and 1:65, typically about 1:53.

The formulation may further include a synergist for the pyrethroid, i.e. a substance capable of enhancing its efficacy and/or spectrum or range of insecticidal or acaricidal efficacy even though the synergist alone may not be considered an insecticide or acaricide. The synergist may, for example, be selected from the group consisting of piperonyl butoxide, bucarpolate, N-octylbicyclohexenedicarboximide, 1,2-methylendioxy-4-(2-octylsulfinyl)-propyl-benzol, propylisome, propynylcarbamate, propinylether, propinyloxime, propinylphosphonate, sesamex, S,S,S-tributylphosphoro-thioate and sulfoxide.

The formulation may typically comprise [percentages given in "m/v"]:

| | |
|---|---|
| pyrethroid | between 0,1 and 10% |
| synergist | between 0,1 and 30% |

| | |
|---|---|
| organophosphate | between 0 and 10% |
| polar solvent | between 0 and 10% |
| fly repellant in the form of non-polar co-solvent | between 0 and 5% |
| vegetable oil | balance to 100%, but at least 70% |

More preferably, however, when the formulation includes an organophosphate, it comprises [relative quantities again expressed in mass to volume percentage]

| | |
|---|---|
| pyrethroid | between 1 and 3% |
| synergist | between 0,1 and 15% |
| organophosphate | between 0,5 and 5% |
| polar solvent | between 0,1 and 10% |
| non-polar solvent | between 0,1 and 10% |
| vegetable oil | balance to 100%, but at least 70% |

EXAMPLES

The invention will now be described by way of the following non-limiting examples and the accompanying FIG. 1 which is more fully defined in Example 9.

EXAMPLE 1

Preparation of Test Formulations According to the Invention

The following components are admixed in the proportions as stated to obtain three different animal pour-on formulations according to the invention.

| | FORMULATION | | |
|---|---|---|---|
| | A | B | C |
| Cypermethrin | 1,0% | 1,0% | 1,0% |
| Alphatethin | 0,5% | 0,5% | 0,5% |
| Piperonyl butoxide | 7,5% | 7,5% | 7,5% |
| Tetrachlorvinphos | 2,0% | 2,0% | — |
| Diacetone alcohol | 5,0% | 5,0% | 5,0% |
| Cymiazol | 2,0% | — | 2,0% |
| Dibutyl phthalate | 5,0% | 5,0% | 5,0% |
| Pure sunflower seed oil | to 100% | to 100% | to 100% |

EXAMPLE 2

Efficacy of the Formulations of the Invention in Comparison to Commercial products and Untreated Control The efficacy of the formulations of the present invention was demonstrated by a trail involving 25 Brahman or Brahman crossed free roaming cattle on a farm where the tick challenge was known to be high. The animals were blocked into 5 groups of five each and randomly allocated to various treatment groups. One of the groups constituted a control group, Group D, and was treated with a commercially available flumethrin-containing ectoparasiticidal formulation [Product D] according to the manufacturer's recommendations. A further group, group E, constituted an untreated control group. Groups A, B and C were respectively treated with Formulations A, B and D as described in Example 1 above.

Before commencement of the treatment all ticks, whether as unengorged male and female and half or fully engorged female ticks, were counted on the group of 25 animals. These counts were total body counts and differentiated the adult ticks by standard recommended groupings for tick identification. Thereafter the animals were again processed through the handling facility and each animal treated according to its allocation in terms of treatment group and specific treatment. The treatments were based on the individual's live mass.

Thereafter tick counts took place weekly on days +7 and +14.

The untreated control group, although it ran with the treated animals, was not given any treatments but these animals were dipped in a commercially available amitraz-based cattle spray before the commencement of the trial.

For the duration of the trial all the animals included in the various treatment groups ran together with other animals as one herd. The total herd size numbered approximately 70 animals. They were thus not separated into different groups and kept apart from each other for the trial as it was not possible to implement this.

All of the pour-on formulations were applied along the topline of the animal from the withers to the base of the tail. The quantities of product were measured in separate graduated measuring containers—one per product. The dosages are tabulated below:

| | Dosage | Volume applied |
|---|---|---|
| Formulation A | 1.5 mpk | 10 ml/100 kg |
| Formulation B | 1.5 mpk | 10 ml/100 kg |
| Formulation C | 1.5 mpk | 10 ml/100 kg |
| Product D | 1.0 mpk | 10 ml/100 kg |

All tick counts that were conducted on the various groups of animals were done by individuals using plastic disposal gloves which were discarded after each animal.

The trial was terminated after the tick counts on day +14.

Results

The results are set out in Tables 1 to 3 below. In the tables N signifies the total number of ticks on the five animals, and % indicates the number of ticks surviving or present after 7 and 14 days respectively expressed as a percentage of the initial infestation.

TABLE 1

EFFECT OF VARIOUS POUR-ON FORMULATIONS ON TOTAL TICK COUNT

| PERIOD POST TREATMENT | ANIMAL GROUPS & TREATMENT | | | | | | | | | |
|---|---|---|---|---|---|---|---|---|---|---|
| | GROUP A FORMULATION A | | GROUP B FORMULATION B | | GROUP C FORMULATION C | | GROUP D FORMULATION D | | GROUP E FORMULATION E | |
| | N | % | N | % | N | % | N | % | N | % |
| Day 0 | 456 | — | 388 | — | 451 | — | 418 | — | 401 | — |
| Day 0 + 7 | 235 | 51.53 | 133 | 34.27 | 189 | 41.9 | 160 | 38.27 | 395 | 98.5 |
| Day 0 + 14 | 213 | 46.71 | 125 | 32.21 | 340 | 75.38 | 163 | 38.99 | 1082 | 269.82 |

TABLE 2
EFFECT OF VARIOUS POUR-ON FORMULATIONS ON BROWN EAR TICK COUNT

| PERIOD POST TREATMENT | GROUP A FORMULATION A | | GROUP B FORMULATION B | | GROUP C FORMULATION C | | GROUP D FORMULATION D | | GROUP E FORMULATION E | |
|---|---|---|---|---|---|---|---|---|---|---|
| | N | % | N | % | N | % | N | % | N | % |
| Day 0 | 79 | — | 39 | — | 51 | — | 65 | — | 61 | — |
| Day 0 + 7 | 193 | 224 | 111 | 284 | 128 | 251 | 144 | 222 | 300 | 492 |
| Day 0 + 14 | 143 | 181 | 74 | 190 | 213 | 418 | 147 | 227 | 844 | 1384 |

TABLE 3
EFFECTIVE OF VARIOUS POUR-ON FORMULATIONS ON BONT TICKS

| PERIOD POST TREATMENT | GROUP A FORMULATION A | | GROUP B FORMULATION B | | GROUP C FORMULATION C | | GROUP D FORMULATION D | | GROUP E FORMULATION E | |
|---|---|---|---|---|---|---|---|---|---|---|
| | N | % | N | % | N | % | N | % | N | % |
| Day 0 | 354 | — | 327 | — | 377 | — | 318 | — | 310 | — |
| Day 0 + 7 | 42 | 12 | 22 | 7 | 60 | 16 | 16 | 5 | 89 | 29 |
| Day 0 + 14 | 70 | 20 | 51 | 16 | 127 | 34 | 16 | 5 | 231 | 75 |

Referring one refers to the tables it will be seen that there was a reasonable tick infestation of all the cattle in the various groups including bont ticks and brown ear ticks prior to treatment. However, at the next tick count one week later, the brown ear tick infestation had climbed significantly. The cattle were re-treated on day 0+7 at the same dosage rates as previously and a final tick count conducted on day 0+14. During the week from day 7 to day 14 there had been extensive rains on the property. The mean bont tick count on day 14 remained constant for the D group and had increased slightly for the group B animals treated with the B formulation. The A formulation showed a very similar trend to that of B formulation but with a slightly higher total bont tick count. The C formulation showed a greater increase in mean bont tick burden and the least level of control of bont ticks in this trial. The untreated control group showed a fairly dramatic rise and more than doubled the mean total bont tick count in the period from day 7 to day 14.

The B formulation, in particular, produced tick control efficacy virtually equivalent to the commercial D formulation and is therefore considered a commercially viable formulation. The other two test formulations were not as effective as the B formulation but nevertheless compared reasonably well with the commercial formulation and has undoubted activity against ticks.

It is significant that none of the treated animals showed any sign of irritancy. Effective control of the brown ear tick is essential in animal husbandry due to physical damage caused by these ticks to the ears of cattle with resultant blood loss. The bont tick serves as a vector for various viral diseases in Africa and its control too is essential for profitable cattle ranching.

EXAMPLE 3

The Efficacy of Formulation B Pour-On for Cattle Against a Natural Field Infestation of House and Stable Flies in a Dairy A field trial was conducted on a group of 80 Jersey diary cattle, 25 heifers and 11 dry cows. The treated animals were split into 2 groups—first the heifer herd and then the milking herd. The 2 treatment groups were kept separately at all times.

All the animals were naturally infested with house flies [*Musca domestica*] and stable flies [*Stomoxys calcitrans*]. The heifer group was treated first on Day 0 with Formulation B at a dosage of 10 ml/100 kg and compared to the untreated milking herd. On day +7 it was decided to treat the milking herd [±80 animals] and compare them against the dry cow herd [±11 animals]. This was done because of the complication of varying weather conditions plus a delay in fly infestation increasing in the heifer after treatment.

The results are shown in Table 4 below.

TABLE 4
FLY TRIAL
AVERAGE FLY COUNTS PER HEAD ON 40 ANIMALS IN 4 REPLICATES OF 10 ANIMALS
FARM: AVERCON

| | | | 18/10 89 | 19/10 89 | 20/10 89 | 23/10 89 TREAT | 24/10 89 | 25/10 89 | 26/10 89 | 27/10 89 | 30/10 | 31/10 89 | 1/11 89 |
|---|---|---|---|---|---|---|---|---|---|---|---|---|---|
| Flies | Treatment | H | 6,28 | 8,78 | 4,7 | 4,43 * | 0,08 | 0,88 | 1,95 | 2,73 | | 1,53 | 1,7 |
| | Group 1 | S | 4,57 | 4,0 | 2,25 | 3,33 * | 0,18 | 0,83 | 0,7 | 1,28 | * | 0,93 | 0,65 |
| | Control | H | 9,82 | 11,00 | 5,68 | 9,78 | 4,68 | 10,13 | 10,25 | 11,58 | TREAT * | 1,03 | 2,8 |
| | Treatment Group 2 | S | 4,33 | 4,85 | 2,88 | 5,35 | 2,35 | 3,78 | 4,9 | 4,65 | * | 0,48 | 0,58 |
| | Untreated Control | H | | | | | | | | | | 4,35 | 2,8 |
| | | S | | | | | | | | | | 2,45 | 1,85 |
| Temperature °C. | | | 28 | 30 | 24 | 21 | 19 | 20 | 26 | 24 | | 28 | 27 |
| Humidity | | | 32 | 35 | 53 | 42 | 54 | 56 | 30 | 53 | | 33 | 28 |
| Wind [mph]. | | | 3–7 | 4–6 | 8–10 | — | 4–6 | 4–6 | 2–4 | 4–6 | | 4–8 | 2–4 |

TABLE 4-continued

FLY TRIAL
AVERAGE FLY COUNTS PER HEAD ON 40 ANIMALS IN 4 REPLICATES OF 10 ANIMALS
FARM: AVERCON

| Cloud % | | | 10 12 h35 | 10 11 h40 | 50 13 h10 | 20 10 h53 | 100 12 h55 | 50 13 h00 | 10 13 h10 | .10 10 h10 | | 10 12 h35 | 90 12 h45 |
|---|---|---|---|---|---|---|---|---|---|---|---|---|---|
| Time | | | | | | 4/11 89 | 6/11 89 | 9/11 89 | 10/11 89 | 13/11 89 | 16/11 89 | 17/11 89 | 20/11 89 | 21/11 89 |
| Flies | Treatment Group 1 | H | 0,68 | 2,35 | 2,03 | 2,75 | 2,9 | 3,0 | 2,8 | 3,68 | 4,65 |
| | | S | 1,33 | 1,6 | 1,78 | 2,0 | 1,63 | 2,33 | 0,62 | 1,83 | 1,98 |
| | Control Treatment Group 2 | H | 0,93 | 2,23 | 2,6 | 3,08 | 2,78 | 4,35 | 9,45 | 7,95 | 8,53 |
| | | S | 0,2 | 1,4 | 2,1 | 1,95 | 2,6 | 3,08 | 1,3 | 3,8 | 4,68 |
| | Untreated Control | H | 1,82 | 3,2 | 3,8 | 7,27 | 5,6 | 4,8 | 4,85 | 7,7 | 7,05 |
| | | S | 0,91 | 2,05 | 3,95 | 4,35 | 4,0 | 3,5 | 1,3 | 3,4 | 5,75 |
| Temperature °C. | | | 20 | 22 | 22 | 26 | 22 | 21 | 21 | 19 | 22 |
| Humidity | | | 63 | 65 | 58 | 48 | 66 | 64 | 32 | 71 | 50 |
| Wind [mph] | | | 7-9 | 2-4 | 6-8 | 2 | — | 2-4 | 6-9 | 2-4 | 2-4 |
| Cloud % | | | 70 | 10 | 70 | 10 | 80 | 80 | 0 | 80 | 0 |
| Time | | | 10 h15 | 13 h00 | 11 h10 | 12 h30 | 11 h25 | 13 h45 | 09 h50 | 11 h10 | 10 h30 |

*On 30/10 the control group was treated and became Treatment Group 2, and a new untreated Control Group was introduced.
S = Stable Flies
H = House Flies From the above table it can be seen that following the first treatment reductions of 99% and 95% were seen in house fly and stable fly numbers respectively. Following the second treatment a reduction of 91% and 90% in house and stable fly numbers could be demonstrated. It was concluded that Formulation B pour-on for cattle was very effective in protecting dairy cattle against two common fly species and that the duration of efficacy was at least one week.

EXAMPLE 4

The Efficacy of Formulation B Pour-On for Cattle Against a Natural Infestation of Red Lice [*Damalinia bovis*]

Twelve [12] Jersey heifers exposed to a moderate natural infestation of red biting lice [*D. bovis*] and to a lower infestation of blue sucking lice [*L. vituli*] were divided into two groups of six animals each. The two groups were kept in separate camps for the trial duration [26 days].

Lice counts were done on the neck only but if found to be zero, over the whole body on Days 0, 7, 13 and 26. Formulation B was applied to the top midline at a dosage of 10 ml/100 kg once on day 0.

The treatment was successful in the eradication of the red lice on the animals. However, blue lice were found on two of the treated animals on Day 8 and on one of the animals on Day 13.

After 68 days it appeared that the treated animals were still free of lice but this inspection was not done by trained scientists.

EXAMPLE 5

The Efficacy of Formulation B Pour-On Dip for Cattle Against the Cattle Louse Fly, *Hippobosca Rufipes*

A trial was conducted on a small herd of Friesland dairy cattle, heavily infested with cattle louse flies, *Hippobosca rufipes* in the Tlakagaing area of Bophuthatswana.

Twenty-four animals [13 cows, 1 ox, 6 calves and 4 horses] were treated once on Day 0 with Formulation B pour-on dip for cattle at a dosage rate of 10 ml per 100 kg body mass as a backline pour on or along the sides.

| Older cows | 60 ml |
|---|---|
| Younger cows | 45 ml |
| Large calves | 30 ml |
| Small calves | 15 ml |
| Horses | 25 ml |

The formulation was applied by walking amongst the herd, which was restrained in a pen, and applying the product by means of a drenching gun to either the top midline or as a squirt along the side of the body. Following treatment the flies went through a short period of excessive biting before dying and dropping off. Approximately 45 minutes after treatment no flies could be detected on any of the cattle. This was again confirmed at a follow up visit on Day 7.

It was concluded that Formulation B was very effective in combatting cattle louse flies with one treatment and that it has a duration of at least 7 days.

EXAMPLE 6

The In Vitro Efficacy of Formulation B Pour-On dip for Cattle Against Sand Tampans [*Ornithodoros Savignyi*]

An in vitro sand tampan exposure trial was conducted at the Terenure Research Centre near Kempton Park.

Sand tampans [*Ornithodoros savignyi*] was obtained from a cattle auction yard. They were caught following $CO_2$ stimulation from dry ice and transported to Terenure in sand.

The objective of the pilot study was to determine the killing effect of Formulation B on sand tampans.

Five tampans each were placed on filter paper, impregnated with Formulation B in petri dishes. They were exposed for 1, 2, 3, 4 and 5 minutes at a time and the extent of mortalities recorded.

It was concluded that sand tampans required a minimum of 4 minutes contact time with Formulation B impregnated filter paper before they died. Since tampans naturally feed for longer than 4 minutes on their hosts, Formulation B should be effective in killing sand tampans infecting cattle under field conditions.

EXAMPLE 7

The Field Efficacy of Formulation B Pour-On Dip for Cattle and Paracide* Cattle Dip Against Sand Tampans [*Ornithodoros savignyi*]

A trial was conducted at a sand tampan infested cattle auction yard.

Four groups comprising of 3 animals each were arbitrarily selected from a herd of Hereford cross steers and heifers. The first group was treated 4 days prior to exposure with Formulation B pour-on dip for cattle at a dosage rate of 10 mls per 100 kg body mass. The second group was treated 2 days before exposure with the same formulation and dosage rate. The third group was sprayed with 5 liters each of a dipwash containing 70 ppm alphamethrin on the same day as the exposure took place. The fourth group served as an untreated control group.

All 12 animals were exposed to sand tampans on Day 0 of the trial. Engorged and half engorged tampans were collected after having dropped off the animals following a 2 hour feeding period. They were transferred to jars and kept in sand for 72 hours following exposure. These tampans were evaluated for mortalities on day +3 of the trial. The percentage mortalities were recorded as follows:

| Formulation B [4 days] | 7.8 |
| Formulation B [2 days] | 20.0 |
| Paracide* | 51.0 |
| Untreated controls | 0 |

It was deducted that a single treatment with Formulation B or Paracide* Cattle Dip, a commercially available product, does not protect cattle against sand tampan challenge. A percentage of sand tampans that have fed on treated animals can however be expected to subsequently die.

EXAMPLE 8

The Efficacy of Formulation B Pour-On Dip for Cattle and Paracide* Cattle Dip [SmithKline] Against Sand Tampans [*Ornithodoros savignyi*]

A small scale trial was conducted in four young Friesland dairy calves at Terenure Research Centre near Kempton Park in South Africa.

The four animals were randomly assigned to 4 groups. Animal No. 443 [=Group 1] was treated with Formulation B pour-on dip for cattle on Day 0 at a dosage rate of 10 ml per 100 kg live mass as a mid backline application. Animal No. 442 [=Group 2] was treated with the same formulation but at a dosage rate of 20 ml per 100 kg body mass. Animal No. P1 [=Group 3] was sprayed with 5l dipwash of an EC containing 70 g/l alphamethrin [Paracide* Cattle Dip—SmithKline] whilst Animal No. 190 [=Group 4] served as an untreated control.

Ten unfed sand tampans were exposed to the back of each animal daily from Day +1 to +7. They were allowed to engorge over a 10 minute period, transferred to petri-dishes and thereafter incubated for 24 hours at 25° C. A percentage engorgement and mortality was recorded immediately and 24 hours post-exposure respectively.

It was concluded that although both formulations had a weak repellancy effect it killed sand tampans effectively for 3 to 4 days after treatment.

EXAMPLE 9

The Efficacy of Formulation B Against Face Flies on Cattle

In a herd of 80 mixed breed cattle the face fly population was allowed to increase over a period of three months to achieve a high mean number of about 10 face flies per animal. A randomly selected test group of 40 of the animals was then treated with formulation B and daily face fly counts were taken for the first week after treatment on both the test and control groups, which groups ran separate from one another after treatment. By the seventh day after treatment the mean fly count on the untreated control group, which had initially dropped in accordance with the known phenomena that treatment resulting in a reduction of the fly load at one locus also causes a reduction [albeit a lesser one] at the untreated locus, had increased again to the initial levels.

Thirty-two of the animals of the control group were then treated with Formulation B.

The immediate knock-down effect of Formulation B and the afterworking thereof in limiting face fly numbers to less than about 20% of the initial fly count number is evident from the graph set out in FIG. 1 which is a graph showing the mean number of face flies against time in respect of three groups of animals [the original control group being split on 10/4 to constitute a new test group].

The Applicants believe that, as a result of the high proportion of vegetable oil carrier, i.e. the high degree of dilution, pesticides which can normally not be used in pure solvent-based pour-on formulations. e.g. due to their skin irritancy, can now be used, e.g. since the oil dilutes the pesticide down to non-irritancy levels on application. Furthermore, the oil ensures good spreadability and low skin penetration activity. The oil still further safeguards against skin irritancy by also acting as a refatting agent for replenishing any skin fat removed by the pesticide and co-solvents. Further, due to the low degree of skin penetration, the pesticide residues in muscle tissue, fat, kidney and lever are extremely low even after repeated application to test animals. Furthermore, the unique combination of active ingredients and selection of solvents constitutes a combination product which is not known in the trade or literature and which exhibits properties which are not offered by any presently known commercial product.

I claim:

1. An animal pour-on pesticidal formulation which comprises at least one pesticide comprising between 0.1% and 10% of a synthetic pyrethroid selected from the group consisting of alphamethrin, allethrin, barthrin, bioresmethrin, biopermethrin, cismethrin, cyclethrin, cypermethrin, cyhalothrin, cyfluthrin, cyphenothrin, deltamethrin, dimethrin, fenpropanate, fenvalerate, flumethrin, flyvalinate, indothrin, permethrin, phenothrin, phthalthrin, resmethrin, tetramethrin, sumithrin, tralomethrin and tralocythrin; between 0% and 10% of an organophosphate selected from the group consisting of tetrachlorvinphos and diazinon; an amidine selected from the group consisting of cymiazol, amitraz and chlormethiuron; between 0.1% and 10% of a synergist selected from the group consisting of piperonyl butoxide, bucarpolate, N-octylbicyclohexenedicarboximide, 1,2-methylendioxy-4-(2-oxtylsulfinyl)-propyl-benzol, propylisone, propinylcarbamate, propinylether, propinyloxime, propinylphosphonate, sesamex, S,S,S-tributylphosphorothioate and sulfoxide; between 0 to 30% of diacetone alcohol as a polar solvent; between 0 and 5.0% of a fly repellant in the form of a non-polar co-solvent selected from the group consisting of dibutylphthalate and stabilene; and at least one vegetable oil consisting of glycerides of carboxylic acids with carbon chain lengths of more than 14 carbon atoms as carrier of the pesticide, said carrier comprising at least 70% m/v of the formulation.

2. The pesticidal formulation of claim 1 wherein the synthetic pyrethroid is cypermethrin.

3. The pesticidal formulation of claim 1 wherein the synthetic pyrethroid is cypermethrin enriched as to the (1R cis)S and (1S cisR) enantiomer isomer pair of alpha-cyano-3-phenoxybenzyl-3-(2,2-dichlorovinyl)-2,2-dimethyl cyclopropane carboxylate.

4. The pesticidal formulation of claim 3 wherein the (1R cis)S and (1S cisR) enantiomer isomer pair of alpha-cyano-3-phenoxybenzyl-3-(2,2-dichlorovinyl)-2,2-cimethylcyclopropane carboxylate constitutes more than 40% by mass of the total of all isomers of that compound present in the formulation.

5. The pesticidal formulation of claim 1 wherein the organophosphate is tetrachlorvinphos and is present in the formulation in an m/v percentage of between 0,5 and 5%.

6. The pesticidal formulation of any one of claims 1 and 2 to 5 wherein the solvent is a mixture of dibutylphthalate and diacetonealcohol which are both present in the formulation in an m/v percentage of between 0.1 and 10%.

7. The pesticidal formulation which comprises a combination of the following ingredients in the mass to volume [m/v] percentages as indicated:

| | |
|---|---|
| alphamethrin enriched cypermethrin | 1.5% |
| piperonylbutoxide | 7.5% |
| tetrachlorvinphos | 2.0% |
| diacetone alcohol | 10.0% |
| dibutylphthalate | 5.0% |
| pure sunflower seed oil | 74% |

8. A method of combatting ectoparasite infestation on an animal host comprising the steps of applying to a localised region of the host an ectoparasiticidally effective amount of formulation of any one of claims 1 to 8.

* * * * *